US009950306B2

(12) United States Patent
Braun et al.

(10) Patent No.: US 9,950,306 B2
(45) Date of Patent: Apr. 24, 2018

(54) PROCESS FOR PRODUCING WATER-ABSORBING POLYMER PARTICLES WITH HIGH FREE SWELL RATE

(75) Inventors: Markus Braun, Heidelberg (DE); Matthias Weismantel, Jossgrund-Oberndorf (DE)

(73) Assignee: BASF SE, Ludwigshafen (DE)

( * ) Notice: Subject to any disclaimer, the term of this patent is extended or adjusted under 35 U.S.C. 154(b) by 240 days.

(21) Appl. No.: 13/544,485

(22) Filed: Jul. 9, 2012

(65) Prior Publication Data

US 2013/0017945 A1    Jan. 17, 2013

Related U.S. Application Data

(60) Provisional application No. 61/507,610, filed on Jul. 14, 2011.

(51) Int. Cl.
| | |
|---|---|
| *C08F 220/06* | (2006.01) |
| *C08F 2/10* | (2006.01) |
| *C08F 230/02* | (2006.01) |
| *B01J 20/26* | (2006.01) |
| *B01J 20/30* | (2006.01) |
| *C08F 220/10* | (2006.01) |
| *C08F 2/26* | (2006.01) |
| *A61L 15/60* | (2006.01) |
| *C08F 222/10* | (2006.01) |

(52) U.S. Cl.
CPC .............. *B01J 20/26* (2013.01); *A61L 15/60* (2013.01); *B01J 20/261* (2013.01); *B01J 20/267* (2013.01); *B01J 20/30* (2013.01); *C08F 2/10* (2013.01); *C08F 2/26* (2013.01); *C08F 220/06* (2013.01); *C08F 220/10* (2013.01); *B01J 2220/68* (2013.01); *C08F 222/1006* (2013.01); *C08F 230/02* (2013.01)

(58) Field of Classification Search
CPC ...... C08F 2/06; C08F 2/10; C08F 2/22; C08F 2/24; C08F 2/26; C08F 2/28; C08F 220/06; C08F 220/10; C08F 30/02; C08F 22/10; C08F 22/105; C08F 230/02; C08F 220/02; C08F 222/1006; A61L 15/60; B01J 2220/68; B01J 20/261; B01J 20/267
See application file for complete search history.

(56) References Cited

U.S. PATENT DOCUMENTS

| | | | |
|---|---|---|---|
| 5,397,845 A | 3/1995 | Rebre et al. | |
| 6,107,358 A | 8/2000 | Harada et al. | |
| 2002/0123588 A1* | 9/2002 | Adam et al. ................. | 526/277 |
| 2010/0130679 A1 | 5/2010 | Jakob et al. | |
| 2010/0331486 A1 | 12/2010 | Klagge et al. | |
| 2011/0009540 A1* | 1/2011 | Terrenoire et al. .......... | 524/145 |
| 2011/0071267 A1 | 3/2011 | Lopez Villanueva et al. | |
| 2011/0257340 A1 | 10/2011 | Herfert et al. | |
| 2012/0232177 A1 | 9/2012 | Lopez Villanueva et al. | |
| 2012/0258851 A1 | 10/2012 | Nakatsuru et al. | |

FOREIGN PATENT DOCUMENTS

| | | | | |
|---|---|---|---|---|
| DE | 10 2006 030557 A1 | 1/2008 | | |
| EP | 1 236 781 A1 | 9/2002 | | |
| EP | 1 760 095 A2 | 3/2007 | | |
| EP | 2 267 038 A1 | 12/2010 | | |
| JP | H1119602 A | 7/1999 | | |
| JP | 2001011412 A | 1/2001 | | |
| WO | WO 2009115607 A1 * | 9/2009 | ........... | C09D 143/02 |
| WO | WO-2011/023572 A1 | 3/2011 | | |
| WO | WO-2011/061315 A1 | 5/2011 | | |
| WO | WO-2011/078298 A1 | 6/2011 | | |
| WO | WO-2011/131526 A1 | 10/2011 | | |

OTHER PUBLICATIONS

English Translation of Kamitou et al (JP 11-199602 A); Jul. 1999.*
Emulsion Polymerization; Wikipedia; Apr. 2009.*
Buchholz, Fredric L., et al. *Modern Superabsorbent Polymer Technology*, "Solution Polymerization: Unit Operations and Their Effect on Product Quality." New York: John Wiley & Sons, Inc., 1998, pp. 71-103.
U.S. Appl. No. 12/861,227, filed Aug. 23, 2010.
U.S. Appl. No. 13/509,446, filed May 11, 2012.
U.S. Appl. No. 13/509,951, filed May 15, 2012.
Third Party Observation submitted Oct. 30, 2013, in international application No. PCT/EP2012/063801.
International Search Report in international application No. PCT/EP2012/063801, dated Sep. 21, 2012.

* cited by examiner

*Primary Examiner* — Karuna P Reddy
(74) *Attorney, Agent, or Firm* — Marshall, Gerstein & Borun LLP

(57) ABSTRACT

A process for producing water-absorbing polymer particles with high free swell rate by polymerizing a monomer solution or suspension comprising an ethylenically unsaturated monomer bearing acid groups, a crosslinker, an initiator and an ethylenically unsaturated ionic surfactant.

8 Claims, No Drawings

PROCESS FOR PRODUCING WATER-ABSORBING POLYMER PARTICLES WITH HIGH FREE SWELL RATE

CROSS-REFERENCE TO RELATED APPLICATIONS

This application claims the benefit of U.S. Provisional Patent Application No. 61/507,610, filed Jul. 14, 2011, incorporated herein by reference in its entirety.

The present invention relates to a process for producing water-absorbing polymer particles with high free swell rate by polymerizing a monomer solution or suspension comprising an ethylenically unsaturated monomer bearing acid groups, a crosslinker, an initiator and an ethylenically unsaturated ionic surfactant.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With an increasing amount of crosslinker, the centrifuge retention capacity (CRC) falls and the absorption under a pressure of 21.0 g/cm² (AUL0.3 psi) passes through a maximum.

To improve the use properties, for example, permeability of the swollen gel bed (SFC) in the diaper and absorption under a pressure of 49.2 g/cm² (AUL0.7 psi), water-absorbing polymer particles are generally surface postcrosslinked. This increases the crosslinking of the particle surface, which can at least partly decouple the absorption under a pressure of 49.2 g/cm² (AUL0.7 psi) and the centrifuge retention capacity (CRC). This surface postcrosslinking can be performed in aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds to at least two carboxylate groups of the water-absorbing polymer particles.

The prior application with reference number PCT/EP2011/055761 teaches the use of comonomers for increasing the free swell rate.

It was an object of the present invention to provide an improved process for producing water-absorbing polymer particles, especially water-absorbing polymer particles with high free swell rate.

The object was achieved by a process for producing water-absorbing polymer particles by polymerizing a monomer solution or suspension comprising
 a) an ethylenically unsaturated monomer which bears acid groups and may be at least partly neutralized,
  b) at least one crosslinker,
  c) at least one initiator,
  d) optionally an ethylenically unsaturated monomer copolymerizable with the monomers mentioned under a) and
  e) optionally one or more water-soluble polymers,
  wherein the monomer solution or suspension comprises at least one ethylenically unsaturated ionic surfactant.

The ethylenically unsaturated ionic surfactants for use in accordance with the invention are interface-active compounds which lower the surface tension of water, preferably below 70 mN/m, more preferably below 68 mN/m, most preferably below 67 mN/m, in each case measured at 23° C. as a 0.103% by weight solution in water.

Ethylenically unsaturated ionic surfactants preferably have an ethylenically unsaturated group, a nonpolar spacer and an ionic end group, preference being given to anionic end groups. Suitable ethylenically unsaturated groups are, for example, allyl ether, vinyl ether, acrylic ester and methacrylic ester groups. A suitable nonpolar spacer is, for example, a polypropylene glycol group. Suitable ionic end groups are, for example, quaternary amine, phosphate and sulfate groups.

Particularly suitable ethylenically unsaturated ionic surfactants are compounds of the general formula (I)

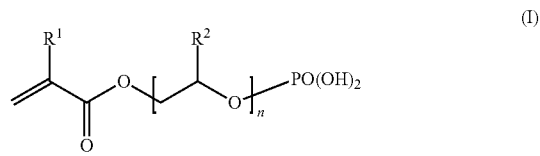

where
 $R^1$ and $R^2$ are each independently hydrogen, methyl or ethyl, preferably methyl or ethyl, most preferably methyl, and
 n is an integer from 3 to 20, preferably from 4 to 15, most preferably from 5 to 10.

The monomer solution or suspension comprises preferably 0.005 to 1% by weight, more preferably from 0.02 to 0.5% by weight and most preferably from 0.05 to 0.2% by weight of ethylenically unsaturated ionic surfactant, based in each case on the unneutralized monomer a).

The present invention is based on the finding that even small amounts of ethylenically unsaturated ionic surfactants distinctly increase the free swell rate (FSR). By virtue of the fact that the ethylenically unsaturated ionic surfactants are incorporated into the polymer network, the influence thereof on the surface tension of the aqueous extract is low.

The amount of ethylenically unsaturated ionic surfactant is typically selected such that the surface tension of the aqueous extract is preferably at least 55 mN/m, more preferably at least 60 mN/m, most preferably at least 65 mN/m.

The reason why use of the ethylenically unsaturated ionic surfactants for use in accordance with the invention nevertheless reduces the surface tension of the aqueous extract might be because a) the conversion of the ethylenically unsaturated ionic surfactants is incomplete and/or b) that the polymerized ethylenically unsaturated ionic surfactants subsequently detach surfactant groups, for example by ester hydrolysis in the case of use of acrylic esters and methacrylic esters.

The water-absorbing polymer particles are produced by polymerizing a monomer solution or suspension, and are typically water-insoluble.

The monomer a) is preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers a) are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The monomer a) typically comprises polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301A1 and DE 103 31 450 A1, mixed acrylates which, as well as acrylate groups, comprise further ethylenically unsaturated groups, as described in DE 103 31 456 A1 and DE 103 55 401A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate, triallylamine and tetraallylammonium chloride.

Very particularly preferred crosslinkers b) are the polyethoxylated and/or -propoxylated glycerols which have been esterified with acrylic acid or methacrylic acid to give di- or triacrylates, as described, for example, in WO 2003/104301A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.2 to 0.5% by weight, based in each case on the unneutralized monomer a). With rising crosslinker content, the centrifuge retention capacity (CRC) falls and the absorption under a pressure of 21.0 g/cm$^2$ (AUL0.3 psi) passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably a mixture of the disodium salt of 2-hydroxy-2-sulfinatoacetic acid, the disodium salt of 2-hydroxy-2-sulfonatoacetic acid and sodium bisulfite (obtainable as Brüggolit® FF6 and Brüggolit® FF7 from Brüggemann Chemicals; Heilbronn; Germany) or the disodium salt of 2-hydroxy-2-sulfinatoacetic acid in pure form (obtainable as Blancolen® HP from Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. It is possible here to combine the process steps of polymerization and drying, as described in WO 2008/040715 A2, WO 2008/052971A1 and WO 2011/026876 A1.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Thereafter, the dried polymer gel is ground and classified, and the apparatus used for grinding may typically be single or multistage roll mills, preferably two or three-stage roll mills, pin mills, hammer mills or vibratory mills.

The mean particle size of the polymer particles removed as the product fraction is preferably at least 200 μm, more preferably from 250 to 600 μm and very particularly from 300 to 500 μm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the permeability (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles of excessively large particle size lower the free swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601A1.

The amount of surface postcrosslinker is preferably 0.001 to 5% by weight, more preferably 0.02 to 2% by weight and most preferably 0.05 to 1% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001 to 1% by weight, preferably 0.005 to 0.5% by weight and more preferably 0.02 to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lodige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; U.S.A.) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

Preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The drying can be effected in the mixer itself, by heating the jacket or blowing in warm air. Equally suitable is a downstream dryer, for example a shelf drier, a rotary tube oven or a heatable screw. It is particularly advantageous to effect mixing and drying in a fluidized bed drier.

Preferred drying temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

In a preferred embodiment of the present invention, the water-absorbing polymer particles are cooled after the thermal drying. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; U.S.A.) and Nara Paddle Cooler (NARA Machinery Europe; Frechen; Germany). Moreover, fluidized bed coolers may also be used.

In the cooler, the water-absorbing polymer particles are cooled to 20 to 150° C., preferably 40 to 120° C., more preferably 60 to 100° C. and most preferably 70 to 90° C.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight, based in each case on the water-absorbing polymer particles. The remoisturizing increases the mechanical stability of the polymer particles and reduces their tendency to static charging. The remoisturizing is advantageously performed in the cooler after the thermal drying.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The present invention further provides the water-absorbing polymer particles obtainable by the process according to the invention.

The inventive water-absorbing polymer particles have a centrifuge retention capacity (CRC) of typically at least 15 g/g, preferably at least 20 g/g, more preferably at least 25 g/g, especially preferably at least 30 g/g and most preferably at least 35 g/g. The centrifuge retention capacity (CRC) of the water-absorbing polymer particles is typically less than 60 g/g.

The inventive water-absorbing polymer particles have an absorption under a pressure of 49.2 g/cm$^2$ (AUL0.7 psi) of typically at least 10 g/g, preferably at least 15 g/g, more preferably at least 20 g/g, especially preferably at least 22 g/g and most preferably at least 23 g/g. The absorption under a pressure of 49.2 g/cm$^2$ (AUL0.7 psi) of the water-absorbing polymer particles is typically less than 30 g/g.

The inventive water-absorbing polymer particles have an absorption under a pressure of 63.0 g/cm$^2$ (AUL0.9 psi) of typically at least 5 g/g, preferably at least 10 g/g, more preferably at least 15 g/g, especially preferably at least 17 g/g and most preferably at least 18 g/g. The absorption under a pressure of 63.0 g/cm$^2$ (AUL0.9 psi) of the water-absorbing polymer particles is typically less than 30 g/g.

The inventive water-absorbing polymer particles have a permeability (SFC) of typically at least $50 \times 10^{-7}$ cm$^3$ s/g, preferably at least $80 \times 10^{-7}$ cm$^3$ s/g, more preferably at least $100 \times 10^{-7}$ cm$^3$ s/g, especially preferably at least $120 \times 10^{-7}$ cm$^3$ s/g, most preferably at least $130 \times 10^{-7}$ cm$^3$ s/g. The permeability (SFC) of the inventive water-absorbing polymer particles is typically less than $250 \times 10^{-7}$ cm$^3$ s/g.

The present invention further provides hygiene articles comprising inventive water-absorbing polymer particles, especially hygiene articles for feminine hygiene, hygiene articles for light and heavy incontinence, diapers or small animal litter.

The production of the hygiene articles is described in the monograph "Modern Superabsorbent Polymer Technology", F. L. Buchholz and A. T. Graham, Wiley-VCH, 1998, pages 252 to 258.

The hygiene articles typically comprise a water-impervious backside, a water-pervious topside and an intermediate absorbent core composed of the inventive water-absorbing polymer particles and fibers, preferably cellulose. The proportion of the inventive water-absorbing polymer particles in the absorbent core is preferably 20 to 100% by weight and more preferably 50 to 100% by weight.

Methods:

The standard test methods described hereinafter and designated "WSP" are described in: "Standard Test Methods for the Nonwovens Industry", 2005 edition, published jointly by the Worldwide Strategic Partners EDANA (Avenue Eugene Plasky, 157, 1030 Brussels, Belgium, www.edana.org) and INDA (1100 Crescent Green, Suite 115, Cary, N.C. 27518, U.S.A., www.inda.org). This publication is available both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Moisture Content

The moisture content of the water-absorbing polymer particles is determined by EDANA recommended test method No. WSP 230.2-05 "Mass Loss Upon Heating".

Centrifuge Retention Capacity

The centrifuge retention capacity (CRC) is determined by EDANA recommended test method No. WSP 241.2-05 "Fluid Retention Capacity in Saline, After Centrifugation".

Absorption Under a Pressure of 21.0 g/cm$^2$ (Absorption Under Load)

The absorption under a pressure of 21.0 g/cm$^2$ (AUL0.3 psi) of the water-absorbing polymer particles is determined by EDANA recommended test method No. WSP 242.2-05 "Absorption under Pressure, Gravimetric Determination".

Extractables

The content of extractables of the water-absorbing polymer particles is determined by EDANA recommended test method No. WSP 270.2-05 "Extractable".

Free Swell Rate

To determine the free swell rate (FSR), 1.00 g ($=W_1$) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker ($=W_2$). The time interval required for the absorption, which has been measured with the stopwatch, is designated as t. The disappearance of the last liquid droplet on the surface is determined as the time t.

The free swell rate (FSR) is calculated therefrom as follows:

$$FSR[g/g\ s]=W_2/(W_1 \times t)$$

If the moisture content of the water-absorbing polymer particles, however, is more than 3% by weight, the weight $W_1$ should be corrected to take account of this moisture content.

Permeability (Saline Flow Conductivity)

The permeability (SFC) of a swollen gel layer under a pressure of 0.3 psi (2070 Pa) is, as described in EP 0 640 330 A1, determined as the gel layer permeability of a swollen gel layer of water-absorbing polymer particles, the apparatus described on page 19 and in FIG. 8 in the aforementioned patent application having been modified such that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The permeability (SFC) is calculated as follows:

SFC[cm³s/g]=(Fg(t=0)×L0)/(d×A×WP)

where Fg(t=0) is the flow of NaCl solution in g/s, which is obtained using linear regression analysis of the Fg(t) data of the flow determinations by extrapolation to t=0, L0 is the thickness of the gel layer in cm, d is the density of the NaCl solution in g/cm³, A is the area of the gel layer in cm², and WP is the hydrostatic pressure over the gel layer in dyn/cm².

Surface Tension of the Aqueous Extract 0.50 g of the water-absorbing polymer particles is weighed into a small beaker, and 40 ml of a 0.9% by weight salt solution are added. The contents of the beaker are stirred with a magnetic stirrer bar at 500 rpm for 3 minutes, then left to settle for 2 minutes. Finally, the surface tension (ST) of the supernatant aqueous phase is measured with a K10-ST digital tensiometer or comparable instrument with a platinum plate (Krüss GmbH, Hamburg, Germany). The measurement is conducted at a temperature of 23° C.

EXAMPLES

The following polymerizable monomers were used:

Sipomer® PAM-100 (RHODIA Opérations, Aubervilliers, France), a polyethylene glycol monomethacrylate phosphate ester with a molecular weight of approx. 400 daltons.

Sipomer® PAM-200 (RHODIA Opérations, Aubervilliers, France), a phosphate ester of a polypropylene glycol monomethacrylate with a molecular weight of approx. 500 daltons.

Sipomer® PAM-300 (RHODIA Opérations, Aubervilliers, France), a phosphate ester of a polypropylene glycol monoacrylate with a molecular weight of approx. 500 daltons.

Sipomer® PAM-4000 (RHODIA Opérations, Aubervilliers, France), a phosphate ester of a hydroxyethyl methacrylate.

Adeka Reasoap® SR-10 (ADEKA Europe GmbH, Düsseldorf, Germany), the ammonium salt of a poly(oxy-1,2-ethanediyl) α-sulfo-ω-[1-(hydroxymethyl)-2-(2-propenyloxy)ethoxy]-$C_{10}/C_{14}$-alkyl ether.

Measurement of Surface Tension 1.03 g of the substance to be analyzed were dissolved in 1.00 l of demineralized water at 23° C. 40 ml of this solution were weighed into a small beaker. The contents of the beaker were stirred with a magnetic stirrer bar at 500 rpm for 3 minutes. Finally, the surface tension of the supernatant aqueous phase is measured with a K10-ST digital tensiometer (Krüss GmbH, Hamburg, Germany). The measurement was conducted at a temperature of 23° C.

| Substance | Surface tension [mN/m] |
|---|---|
| demineralized water | 72.0 |
| Span ® 20 | 50.8 |
| Sipomer ® PAM 100 | 71.2 |
| Sipomer ® PAM 200 | 63.5 |
| Sipomer ® PAM 300 | 60.4 |
| Sipomer ® PAM 4000 | 71.2 |
| Adeka Reasoap ® SR-10 | 65.0 |

-continued

| Substance | Surface tension [mN/m] |
|---|---|
| NaAMPS*[)] | 72.3 |
| MPEGMA**[)] | 70.0 |

*[)]sodium salt of 2-acrylamido-2-methylpropanesulfonic acid
**[)]methoxy polyethylene glycol-2000 methacrylate Production of the Base Polymers:

Example 1 (Comparative Example)

An LUK 8.0K2 kneader with two sigma shafts (Coperion Werner & Pfleiderer GmbH & Co. KG, Stuttgart, Germany) was inertized by purging with nitrogen and then initially charged with a mixture, which had been freed of oxygen by sparging with nitrogen, of 4786.99 g of a 37.3% by weight sodium acrylate solution, 514.45 g of acrylic acid and 522.95 g of demineralized water. Subsequently, 6.9 g of triethoxylated glyceryl triacrylate (purity approx. 85% by weight) dissolved in 100.0 g of acrylic acid as an internal crosslinker and, thereafter, as an initiator, 11.89 g of a 15% by weight aqueous sodium persulfate solution and 1.32 g of a 3% by weight aqueous hydrogen peroxide solution were added. Subsequently, 19.82 g of a 0.5% by weight aqueous ascorbic acid solution were added. The kneader was operated at 96 revolutions per minute in one shaft and at 48 revolutions per minute in the other shaft. Immediately after addition of the ascorbic acid solution, the solution was heated by means of passage of heating fluid (80° C.) through the heating mantle of the kneader. As soon as the temperature in the kneader ceased to rise, the heating was ended and the polymer gel was kneaded for a further 13 minutes. Subsequently, the gel was cooled to about 63° C. and then removed from the kneader. The gel, in portions of 1080 g, was distributed homogeneously on grids and dried in a forced air drying cabinet at 175° C. for 90 min. Subsequently, the dried gel was dried on an LRC 125/70 roll mill (Bauermeister Zerkleinerungstechnik GmbH, Norderstedt, Germany) with successive gap width settings of 1000 μm, 600 μm and 400 μm. The water-absorbing polymer particles were sieved and the resulting sieve fractions were blended so as to obtain the following particle size distribution:

| | |
|---|---|
| >710 μm | 0% by weight |
| 600-710 μm | 13.3% by weight |
| 500-600 μm | 23.3% by weight |
| 300-500 μm | 43.6% by weight |
| 150-300 μm | 19.8% by weight |
| <150 μm | 0% by weight. |

The resulting mixture is homogenized in a 5 l metal vessel in an ELTE 650 ST drum hoop mixer (J. Engelsmann AG, Ludwigshafen, Germany).

The resulting water-absorbing polymer particles were analyzed. The results are summarized in Table A.

Example 2

Example 1 was repeated. In addition, 0.10 g of Adeka Reasoap® SR-10 was dissolved in the monomer solution.

The resulting water-absorbing polymer particles were analyzed. The results are summarized in Table A.

Example 3

Example 1 was repeated. In addition, 0.20 g of Adeka Reasoap® SR-10 was dissolved in the monomer solution.

The resulting water-absorbing polymer particles were analyzed. The results are summarized in Table A.

Example 4

Example 1 was repeated. In addition, 0.50 g of Adeka Reasoap® SR-10 was dissolved in the monomer solution.
The resulting water-absorbing polymer particles were analyzed. The results are summarized in Table A.

Example 5

Example 1 was repeated. In addition, 1.00 g of Adeka Reasoap® SR-10 was dissolved in the monomer solution.
The resulting water-absorbing polymer particles were analyzed. The results are summarized in Table A.

Example 6 (Comparative Example)

Example 1 was repeated. In addition, 2.00 g of Sipomer® PAM 100 were dissolved in the monomer solution.
The resulting water-absorbing polymer particles were analyzed. The results are summarized in Table A.

Example 7

Example 1 was repeated. In addition, 1.00 g of Sipomer® PAM 200 was dissolved in the monomer solution.
The resulting water-absorbing polymer particles were analyzed. The results are summarized in Table A.

Example 8

Example 1 was repeated. In addition, 2.00 g of Sipomer® PAM 200 were dissolved in the monomer solution.
The resulting water-absorbing polymer particles were analyzed. The results are summarized in Table A.

Example 9

Example 1 was repeated. In addition, 3.00 g of Sipomer® PAM 200 were dissolved in the monomer solution.
The resulting water-absorbing polymer particles were analyzed. The results are summarized in Table A.

Example 10

Example 1 was repeated. In addition, 4.00 g of Sipomer® PAM 200 were dissolved in the monomer solution.
The resulting water-absorbing polymer particles were analyzed. The results are summarized in Table A.

Example 11

Example 1 was repeated. In addition, 10.00 g of Sipomer® PAM 200 were dissolved in the monomer solution.
The resulting water-absorbing polymer particles were analyzed. The results are summarized in Table A.

Example 12

Example 1 was repeated. In addition, 1.00 g of Sipomer® PAM 300 was dissolved in the monomer solution.
The resulting water-absorbing polymer particles were analyzed. The results are summarized in Table A.

Example 13

Example 1 was repeated. In addition, 2.00 g of Sipomer® PAM 300 were dissolved in the monomer solution.
The resulting water-absorbing polymer particles were analyzed. The results are summarized in Table A.

Example 14

Example 1 was repeated. In addition, 2.00 g of Sipomer® PAM 4000 were dissolved in the monomer solution.
The resulting water-absorbing polymer particles were analyzed. The results are summarized in Table A.

Example 15 (Comparative Example)

Example 1 was repeated. In addition, 2.00 g of methoxy polyethylene glycol-2000 methacrylate (MPEGMA) were dissolved in the monomer solution.
The resulting water-absorbing polymer particles were analyzed. The results are summarized in Table A.

Example 16 (Comparative Example)

Example 1 was repeated. In addition, 2.00 g of the sodium salt of 2-acrylamido-2-methylpropanesulfonic acid (NaAMPS) were dissolved in the monomer solution.
The resulting water-absorbing polymer particles were analyzed. The results are summarized in Table A.

Example 17 (Comparative Example)

Example 1 was repeated. Instead of 522.95 g of demineralized water, only 425.93 g of demineralized water were initially charged into the reactor, and 99 g of a 2% aqueous, nitrogen-degassed solution of sorbitan monododecanoate (Span® 20) were added with the initiator solution.
The resulting water-absorbing polymer particles were analyzed. The results are summarized in Table A.

TABLE A

Composition of the base polymers.

| Ex. | Comonomer | Amount [% by wt.] | CRC [g/g] | AUL0.3 psi [g/g] | Moisture content [% by wt.] | Extractables [% by wt.] |
|---|---|---|---|---|---|---|
| 1*) | none | — | 35.5 | 16.0 | 1.0 | 10.6 |
| 2 | Adeka Reasoap ® SR-10 | 0.005 | 34.9 | 20.8 | 1.3 | 9.6 |
| 3 | Adeka Reasoap ® SR-10 | 0.01 | 36.5 | 18.6 | 0.5 | 9.8 |
| 4 | Adeka Reasoap ® SR-10 | 0.025 | 33.7 | 24.1 | 1.2 | 9.4 |
| 5 | Adeka Reasoap ® SR-10 | 0.05 | 34.3 | 25.0 | 0.9 | 8.6 |
| 6*) | Sipomer ® PAM 100 | 0.10 | 34.0 | 21.5 | 1.5 | 9.0 |
| 7 | Sipomer ® PAM 200 | 0.05 | 35.6 | 20.1 | 0.9 | 9.4 |
| 8 | Sipomer ® PAM 200 | 0.10 | 35.1 | 23.1 | 0.8 | 9.2 |
| 9 | Sipomer ® PAM 200 | 0.15 | 33.6 | 25.9 | 0.8 | 8.4 |
| 10 | Sipomer ® PAM 200 | 0.20 | 33.8 | 23.3 | 1.2 | 8.5 |
| 11 | Sipomer ® PAM 200 | 0.50 | 32.4 | 26.9 | 1.2 | 7.9 |
| 12 | Sipomer ® PAM 300 | 0.05 | 34.7 | 23.1 | 0.7 | 8.9 |
| 13 | Sipomer ® PAM 300 | 0.10 | 35.2 | 17.9 | 1.6 | 8.8 |

TABLE A-continued

Composition of the base polymers.

| Ex. | Comonomer | Amount [% by wt.] | CRC [g/g] | AUL0.3 psi [g/g] | Moisture content [% by wt.] | Extract- ables [% by wt.] |
|---|---|---|---|---|---|---|
| 14*) | Sipomer ® PAM 4000 | 0.10 | 33.7 | 24.5 | 0.8 | 8.6 |
| 15*) | MPEGMA | 0.10 | 36.0 | 19.1 | 0.7 | 9.7 |
| 16*) | NaAMPS | 0.10 | 35.4 | 17.0 | 1.3 | 9.0 |
| 17*) | Span ® 20**) | — | 34.4 | 19.1 | 0.7 | 8.2 |

*)comparative example
**)not a comonomer

Surface postcrosslinking in the presence of an additional surfactant:

Example 18 (Comparative Example)

For surface postcrosslinking, 1200 g of the base polymer from example 1 were coated in a Pflugschar® M5 plowshare mixer with heating jacket (Gebr. Lödige Maschinenbau GmbH, Paderborn, Germany) at 23° C. and a shaft speed of 200 revolutions per minute by means of a two-substance spray nozzle with the following solution (based in each case on the base polymer):

```
0.992% by weight of isopropanol
 0.14% by weight of a solution of 50% by weight of 1,3-propanediol
              and 50% by weight of N-(2-hydroxyethyl)-2-
              oxazolidinone
0.248% by weight of demineralized water
 0.70% by weight of 1,2-propanediol
 0.50% by weight of a 22% by weight aqueous aluminum lactate
              solution
 0.20% by weight of a 2% by weight aqueous solution of sorbitan
              monococoate
```

After the spray application, the shaft speed was reduced to 50 revolutions per minute and the product was brought to a product temperature of 185° C. by increasing the temperature of the heating jacket (temperature of the heating liquid 238° C.). A total of 10 samples, each of about 20 g, were taken from the reaction mixture, one every 5 minutes, beginning with the attainment of the product temperature of 185° C. The samples were each allowed to cool to 23° C. and sieved off at 710 μm, and the <710 μm fraction was used.

The resulting surface postcrosslinked water-absorbing polymer particles were analyzed. The results for the comparable samples with a CRC of approx. 27 g/g are summarized in table B.

Example 19

Example 18 was repeated with 1200 g of the base polymer from example 3.

The resulting surface postcrosslinked water-absorbing polymer particles were analyzed. The results for the comparable samples with a CRC of approx. 27 g/g are summarized in table B.

Example 20

Example 18 was repeated with 1200 g of the base polymer from example 4.

The resulting surface postcrosslinked water-absorbing polymer particles were analyzed. The results for the comparable samples with a CRC of approx. 27 g/g are summarized in table B.

Example 21

Example 18 was repeated with 1200 g of the base polymer from example 5.

The resulting surface postcrosslinked water-absorbing polymer particles were analyzed. The results for the comparable samples with a CRC of approx. 27 g/g are summarized in table B.

Example 22 (Comparative Example)

Example 18 was repeated with 1200 g of the base polymer from example 6.

The resulting surface postcrosslinked water-absorbing polymer particles were analyzed. The results for the comparable samples with a CRC of approx. 27 g/g are summarized in table B.

Example 23

Example 18 was repeated with 1200 g of the base polymer from example 8.

The resulting surface postcrosslinked water-absorbing polymer particles were analyzed. The results for the comparable samples with a CRC of approx. 27 g/g are summarized in table B.

Example 24

Example 18 was repeated with 1200 g of the base polymer from example 13.

The resulting surface postcrosslinked water-absorbing polymer particles were analyzed. The results for the comparable samples with a CRC of approx. 27 g/g are summarized in table B.

TABLE B

Composition of the polymers after surface postcrosslinking with additional surfactant.

| Ex. | Comonomer | Amount [% by wt.] | CRC [g/g] | FSR [g/(g s)] | SFC [(cm$^3$ s)/ 10$^7$ g)] | ST [mN/m] |
|---|---|---|---|---|---|---|
| 18*) | none | — | 27.7 | 0.31 | 137 | 72.4 |
| 19 | Adeka Reasoap ® SR-10 | 0.01 | 27.5 | 0.39 | 138 | 64.2 |
| 20 | Adeka Reasoap ® SR-10 | 0.025 | 26.7 | 0.41 | 126 | 61.9 |
| 21 | Adeka Reasoap ® SR-10 | 0.05 | 26.4 | 0.51 | 127 | 56.4 |
| 22*) | Sipomer ® PAM 100 | 0.10 | 27.2 | 0.34 | 152 | 72.7 |
| 23 | Sipomer ® PAM 200 | 0.10 | 27.3 | 0.42 | 112 | 69.2 |
| 24 | Sipomer ® PAM 300 | 0.10 | 26.8 | 0.50 | 123 | 56.5 |

*)comparative example

The results show that the surfactant monomers distinctly increase the free swell rate (FSR) and at the same time lower the surface tension.

Sipomer® PAM 200 achieved the best results, i.e. a high free swell rate and only a small lowering of the surface tension. It is possible that surfactant groups can be detached from the polymer by hydrolysis. In this case, the less hydrolysis-sensitive methacrylic esters (such as Sipomer® PAM 200) are superior to the less hydrolysis-stable acrylic esters (such as Sipomer® PAM 300). In addition, sufficient reactivity of the monomer used is also important. For instance, allyl ethers (such as Adeka Reasoap® SR-10) have a much lower reactivity, and so the water-absorbing polymer particles produced therewith also comprise unconverted monomer.

Surface postcrosslinking in the absence of an additional surfactant:

Example 25 (Comparative Example)

For surface postcrosslinking, 1200 g of the base polymer from example 1 were coated in a Pflugschar® M5 plowshare mixer with heating jacket (Gebr. Lodige Maschinenbau GmbH, Paderborn, Germany) at 23° C. and a shaft speed of 200 revolutions per minute by means of a two-substance spray nozzle with the following solution (based in each case on the polymer):

```
0.992% by weight of isopropanol
 0.14% by weight of a solution of 50% by weight of 1,3-propanediol
        and 50% by weight of N-(2-hydroxyethyl)-2-
        oxazolidinone
0.448% by weight of demineralized water
 0.70% by weight of 1,2-propanediol
 0.50% by weight of a 22% by weight aqueous aluminum lactate
        solution
```

After the spray application, the shaft speed was reduced to 50 revolutions per minute and the product was brought to a product temperature of 185° C. by increasing the temperature of the heating jacket (temperature of the heating liquid 238° C.). A total of 10 samples, each of about 20 g, were taken from the reaction mixture, one every 5 minutes, beginning with the attainment of the product temperature of 185° C. The samples were each allowed to cool to 23° C. and sieved off at 710 μm, and the <710 μm fraction was used.

The resulting surface postcrosslinked water-absorbing polymer particles were analyzed. The results for the comparable samples with a CRC of approx. 27 g/g are summarized in table C.

Example 26

Example 25 was repeated with 1200 g of the base polymer from example 2.

The resulting surface postcrosslinked water-absorbing polymer particles were analyzed. The results for the comparable samples with a CRC of approx. 27 g/g are summarized in table C.

Example 27

Example 25 was repeated with 1200 g of the base polymer from example 3.

The resulting surface postcrosslinked water-absorbing polymer particles were analyzed. The results for the comparable samples with a CRC of approx. 27 g/g are summarized in table C.

Example 28

Example 25 was repeated with 1200 g of the base polymer from example 5.

The resulting surface postcrosslinked water-absorbing polymer particles were analyzed. The results for the comparable samples with a CRC of approx. 27 g/g are summarized in table C.

Example 29 (Comparative Example)

Example 25 was repeated with 1200 g of the base polymer from example 6.

The resulting surface postcrosslinked water-absorbing polymer particles were analyzed. The results for the comparable samples with a CRC of approx. 27 g/g are summarized in table C.

Example 30

Example 25 was repeated with 1200 g of the base polymer from example 7.

The resulting surface postcrosslinked water-absorbing polymer particles were analyzed. The results for the comparable samples with a CRC of approx. 27 g/g are summarized in table C.

Example 31

Example 25 was repeated with 1200 g of the base polymer from example 8.

The resulting surface postcrosslinked water-absorbing polymer particles were analyzed. The results for the comparable samples with a CRC of approx. 27 g/g are summarized in table C.

Example 32

Example 25 was repeated with 1200 g of the base polymer from example 9.

The resulting surface postcrosslinked water-absorbing polymer particles were analyzed. The results for the comparable samples with a CRC of approx. 27 g/g are summarized in table C.

Example 33

Example 25 was repeated with 1200 g of the base polymer from example 10.

The resulting surface postcrosslinked water-absorbing polymer particles were analyzed. The results for the comparable samples with a CRC of approx. 27 g/g are summarized in table C.

Example 34

Example 25 was repeated with 1200 g of the base polymer from example 11.

The resulting surface postcrosslinked water-absorbing polymer particles were analyzed. The results for the comparable samples with a CRC of approx. 27 g/g are summarized in table C.

Example 35 (Comparative Example)

Example 25 was repeated with 1200 g of the base polymer from example 14.

The resulting surface postcrosslinked water-absorbing polymer particles were analyzed. The results for the comparable samples with a CRC of approx. 27 g/g are summarized in table C.

Example 36

Example 25 was repeated with 1200 g of the base polymer from example 12.

The resulting surface postcrosslinked water-absorbing polymer particles were analyzed. The results for the comparable samples with a CRC of approx. 27 g/g are summarized in table C.

Example 37

Example 25 was repeated with 1200 g of the base polymer from example 13.

The resulting surface postcrosslinked water-absorbing polymer particles were analyzed. The results for the comparable samples with a CRC of approx. 27 g/g are summarized in table C.

Example 38 (Comparative Example)

Example 25 was repeated with 1200 g of the base polymer from example 15.

The resulting surface postcrosslinked water-absorbing polymer particles were analyzed. The results for the comparable samples with a CRC of approx. 27 g/g are summarized in table C.

Example 39 (Comparative Example)

Example 25 was repeated with 1200 g of the base polymer from example 16.

The resulting surface postcrosslinked water-absorbing polymer particles were analyzed. The results for the comparable samples with a CRC of approx. 27 g/g are summarized in table C.

Example 40 (Comparative Example)

Example 25 was repeated with 1200 g of the base polymer from example 17.

The resulting surface postcrosslinked water-absorbing polymer particles were analyzed. The results for the comparable samples with a CRC of approx. 27 g/g are summarized in table C.

TABLE C

Composition of the polymers after surface postcrosslinking without additional surfactant.

| Ex. | Comonomer | Amount [% by wt.] | CRC [g/g] | FSR [g/(g s)] | SFC [(cm³ s)/ 10⁷ g]] | ST [mN/m] |
|---|---|---|---|---|---|---|
| 25*) | none | — | 27.6 | 0.38 | 98 | 72.5 |
| 26 | Adeka Reasoap ® SR-10 | 0.005 | 27.2 | 0.37 | 120 | 66.5 |
| 27 | Adeka Reasoap ® SR-10 | 0.01 | 26.9 | 0.48 | 97 | 64.2 |
| 28 | Adeka Reasoap ® SR-10 | 0.05 | 26.9 | 0.54 | 104 | 57.8 |
| 29*) | Sipomer ® PAM 100 | 0.10 | 27.3 | 0.38 | 74 | 72.0 |
| 30 | Sipomer ® PAM 200 | 0.05 | 26.7 | 0.36 | 129 | 71.5 |
| 31 | Sipomer ® PAM 200 | 0.10 | 26.9 | 0.43 | 146 | 71.0 |
| 32 | Sipomer ® PAM 200 | 0.15 | 26.7 | 0.47 | 115 | 70.6 |
| 33 | Sipomer ® PAM 200 | 0.20 | 27.2 | 0.42 | 87 | 69.1 |
| 34 | Sipomer ® PAM 200 | 0.50 | 27.0 | 0.45 | 76 | 65.8 |
| 35*) | Sipomer ® PAM 4000 | 0.10 | 27.0 | 0.38 | 93 | 72.3 |
| 36 | Sipomer ® PAM 300 | 0.05 | 27.3 | 0.50 | 96 | 64.2 |
| 37 | Sipomer ® PAM 300 | 0.10 | 26.8 | 0.52 | 165 | 57.9 |
| 38*) | MPEGMA | 0.10 | 27.7 | 0.34 | 113 | 68.5 |
| 39*) | NaAMPS | 0.10 | 27.7 | 0.39 | 103 | 72.0 |
| 40*) | Span ® 20**) | — | 26.8 | 0.54 | 102 | 54.8 |

*)comparative example
**)not a comonomer

The results likewise show that the surfactant monomers distinctly increase the free swell rate (FSR) and at the same time lower the surface tension.

The noninventive comonomers (such as MPEGMA and NaAMPS) have only a minor influence, both on the free swell rate (FSR) and on the surface tension. Nonpolymerized surfactants (such as Span® 20) lower the surface tension too much.

The invention claimed is:

1. A process for producing water-absorbing polymer particles by polymerizing an aqueous monomer solution or suspension comprising
   a) at least one ethylenically unsaturated monomer which bears an acid group and is at least partly neutralized consisting essentially of acrylic acid neutralized to an extent of 25 to 95 mol %,
   b) at least one crosslinker,
   c) at least one initiator,
   d) optionally one or more water-soluble polymer,
   wherein the monomer solution comprises 0.005 to 1%, by weight, of at least one ethylenically unsaturated anionic surfactant having an ethylenically unsaturated group, a polypropylene glycol group as a nonpolar spacer, and a phosphate as an anionic group, and
   the polymerization is a solution polymerization,
   and the polymer particles having a centrifuge retention capacity of at least 15 g/g.

2. The process according to claim 1, wherein the ethylenically unsaturated group in the ethylenically unsaturated anionic surfactant is an allyl ether, vinyl ether, acrylic ester, or methacrylic ester group.

3. The process according to claim 1, wherein the ethylenically unsaturated anionic surfactant is a compound of the general formula (I)

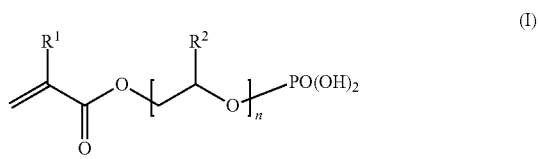

where R¹ is hydrogen, methyl, or ethyl, R² is methyl, and n is an integer from 3 to 20.

4. The process according to claim 1, wherein the aqueous monomer solution, based on the unneutralized monomer a), comprises from 0.05 to 0.2% by weight of the ethylenically unsaturated anionic surfactant.

5. The process according to claim 1, wherein monomer a) has been neutralized to an extent of 30 to 80 mol %.

6. The process according to claim 1, wherein the aqueous monomer solution, based on the unneutralized monomer a), comprises from 0.1 to 1% by weight of the crosslinker b).

7. The process of claim 1 wherein the aqueous monomer solution, based on the unneutralized monomer a), comprises from 0.02 to 0.5% by weight of the ethylenically unsaturated anionic surfactant.

8. The process of claim 1 wherein the aqueous monomer solution, based on the unneutralized monomer a), comprises from 0.05 to 1% by weight of the ethylenically unsaturated anionic surfactant.

* * * * *